(12) United States Patent
Cusack et al.

(10) Patent No.: US 6,493,724 B1
(45) Date of Patent: Dec. 10, 2002

(54) WEB-INTEGRATED INVENTORY MANAGEMENT SYSTEM AND METHOD

(75) Inventors: Martin V. Cusack, Boca Raton, FL (US); Jaime Pereira, Boca Raton, FL (US); Bruce R. Seidenstein, Del Ray Beach, FL (US)

(73) Assignee: Biosample.com, Inc., Boca Raton, FL (US)

( * ) Notice: Subject to any disclaimer, the term of this patent is extended or adjusted under 35 U.S.C. 154(b) by 283 days.

(21) Appl. No.: 09/597,484

(22) Filed: Jun. 19, 2000

(51) Int. Cl.[7] ................... G06F 17/30; G06F 17/60
(52) U.S. Cl. ......................... 707/104.1; 705/10
(58) Field of Search ................. 707/10, 104.1; 705/26, 10; 435/2

(56) References Cited

U.S. PATENT DOCUMENTS

| | | | |
|---|---|---|---|
| 5,920,871 A | * 7/1999 | Macri et al. | 707/104.1 |
| 5,960,411 A | * 9/1999 | Hartman et al. | 345/962 |
| 5,993,387 A | * 11/1999 | Moore et al. | 435/2 |
| 6,338,050 B1 | * 1/2002 | Conklin et al. | 705/26 |
| 6,366,682 B1 | * 4/2002 | Hoffman et al. | 382/115 |
| 6,366,924 B1 | * 4/2002 | Parce | 422/62 |

* cited by examiner

*Primary Examiner*—Wayne Amsbury
*Assistant Examiner*—Nguyen Camlinh
(74) *Attorney, Agent, or Firm*—Jacobson Holman PLLC

(57) ABSTRACT

An e-commerce exchange for gathering and managing a widely distributed inventory of blood, tissue and other samples for the biomedical research community and pharmaceutical industries worldwide. Samples belonging to registered sample providers are entered into a database at a central host site which is part of a distributed computer network. The samples are tagged by fields to cross reference the samples according to a number of specified criteria. Registered buyers search the database according to desired criteria. When the criteria of the search request matches the criteria specified for a particular sample, the central host site approves and supervises transfer of the particular sample from the supplier to the requesting buyer. Additionally, when the search request is not successful, there being no matching sample, the buyer may enter the requested sample criteria onto a wish list. A sample supplier having an unlisted sample meeting the criteria of an biological sample on the wish list may enter the sample into the database and the central host site will notify the buyer of sample availability and prompt transfer to the buyer.

19 Claims, 11 Drawing Sheets

| SAMPLES | WISH LIST | SHOPPING CART | ORDERS | ACCOUNT SERVICES |

LOG OFF

New Sample

Required Fields are designated by Bold face field titles.

INVENTORY

SEARCH

GLOSSARY

PRODUCTS

HELP

The BIG PICTURE
Click here to read an overview of the system.

Sample Information

Volume [ ] ● mL ○ gr.          ☐ Bulk Sample

Matrix [ ▼ ]          Price [ ] *in US$*

Lab Id [ ]          per ● sample
                         ○ unit of measure

Product 1

Name [ ]
● Product ○ Diagnosis ○ Drug

Value [ ] *(optional < or >)*     Tested [ ▼ ]

Test Manufacturer [ ] [Select]

Product 2

Name [ ]
● Product ○ Diagnosis ○ Drug

Value [ ] *(optional < or >)*     Tested [ ▼ ]

Test Manufacturer [ ] [Select]

⎫
⎬ 15
⎭

Patient Information

Age [ ]          Race [ ▼ ]

Gender [ ▼ ]

Patient Id [ ]          ☐ Medical Record Available

Birth Date [ ] *yyyy-mm-dd*     ☐ Doctor Certified

Field of Medicine [ ▼ ]

⎫
⎬ 17
⎭

Oncology Information

Site [ ]          Stage [ ]

Grade [ ]          Status [ ]

⎫
⎬ 19
⎭

21 — [ADD]                    [Clear Form]

FIG. 6

WEB-INTEGRATED INVENTORY MANAGEMENT SYSTEM AND METHOD

BACKGROUND OF THE INVENTION

1. Field of the Invention

The present invention is related to the field of on-line computing and, more particularly, to a computer-based system and method for managing a dynamic and widely distributed inventory of biological samples or other perishable items and materials.

2. Description of the Related Art

To date, scientists and clinical researchers have spent valuable time and resources searching for the biological samples, such as blood, tissue, serum, plasma, bodily fluids, etc., that are essential to allow them to research, diagnose and help expedite cures for the world's vast number of diseases and other medical conditions.

Research sample needs are currently only partially fulfilled and are conducted by telephone, facsimile and time consuming networking between sample providers such as doctors, hospitals, laboratories, collection agencies and research product brokers. Using current methods, it often takes weeks to obtain even basic research samples; the procurement of rare samples can take months and even years, if they can be obtained at all.

Accordingly, there is an unmet need and increasing demand in the biomedical/pharmaceutical industry for accessible research products and related data.

SUMMARY OF THE INVENTION

In view of the foregoing, one object of the present invention is to overcome the difficulty in obtaining the biological samples necessary for research and other medical developments through a web-integrated inventory management system.

Another object of the invention is a sophisticated, yet simple to operate, one stop e-commerce exchange.

A further object of the invention is a search engine capable of searching for and locating samples according to a multitude of parameters which could not previously be designated on sample inventories.

A still further object of the invention is an inventory management system allowing sample providers to post their inventory in seconds and obtain worldwide exposure.

Yet another object of the invention is an on-line inventory management system that gives biomedical companies the ability to manage their inventories from designated and secure shelf space accessible to them through any web-enabled computer.

Another object of the invention is an integrated system for searching, finding, purchasing and receiving biological samples in a convenient, cost-effective and timely manner.

In accordance with this and other objects, the present invention is directed to a system and method for use with a distributed computer network, such as the Internet, that enables researchers, and others, to search for and purchase samples of biological material according to specified criteria. Through the present invention, sample buyers and sellers are brought together to a degree not previously available, increasing the value of the samples, both in terms of purchase price and research contribution.

The web-integrated inventory management (WIM) system of the present invention comprises a central host site having a search engine for accessing at least one central host site database. Each sample provider wishing to subscribe to the WIM system provides the central host site with information describing an inventory of biological samples belonging to the sample provider. Each biological sample is tagged according to a plurality of fields. The fields identify the sample by specifying various criteria for or parameters of the sample. Tagging the samples by field essentially indexes the samples, cross-referencing them according to the specified parameters. The field information associated with each sample is then entered into the central host site database.

As the sample provider obtains additional samples, the sample provider can key in these later samples by hand, tagging the fields as desired. Alternatively, the sample provider can send the sample information to the central host site for tagging and entry of the sample into the central host site database.

By subscribing to the WIM system, sample providers may be relieved of the need to manage their own inventory and can instead choose to rely upon the monitoring and updating services provided by the WIM system. Each subscribing sample provider is afforded a designated password-protected "shelf space" with which they can do as they wish, providing them with what is essentially a worldwide storefront window and at very low cost to them. Because the inventory management system is web integrated, sample providers can access their inventories from any location having Internet access.

Researchers and other sample buyers search the WIM system database by specifying desired criteria by field. The WIM search engine searches the central web site database for matches to the request according to the information provided in the tagged fields. If a sample matching the request is not available, the buyer can place the request on a listing of desired but currently unavailable samples, i.e., a wish list. Responsive to a posting on the wish list, the WIM host site automatically generates email messages to subscribing sample providers, informing the sample providers of the desired criteria and that a prospective buyer has posted a request to purchase a sample meeting these criteria.

If a sample provider has, or subsequently obtains, a sample matching the criteria of a wish list item, the sample may be added to that provider's inventory as a new sample. The WIM host site automatically and routinely compares existing inventory sample data to items listed on the wish list. Upon detecting a match between the new sample and a specific wish list request item, the WIM host site generates an email notifying the buyer that a sample meeting his or her wish list criteria is available, and prompts purchase.

If a sample meeting all the specified criteria is available, the buying sequence may be initiated. This sequence is commenced by the buyer requesting availability of the sample. Responsive to this request, the WIM host site generates an email to the appropriate sample provider. The email includes a hyperlink to the host site. The sample provider confirms sample availability by clicking on the hyperlink and then checking which samples are available. The WIM host site then generates and sends an email to the buyer identifying the confirmed samples.

To purchase, the buyer selects a form of purchase, e.g., purchase order, wire, credit card, etc. Upon approval of the order by the central host site, a confirmation is sent to the buyer and to the sample provider, and the order is shipped.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 6 is an illustrative data entry screen for adding a new sample, in accordance with the present invention.

FIG. 8 is a more detailed flowchart of the sample search process of FIG. 7;

DETAILED DESCRIPTION OF THE PREFERRED EMBODIMENTS

Figure 1:
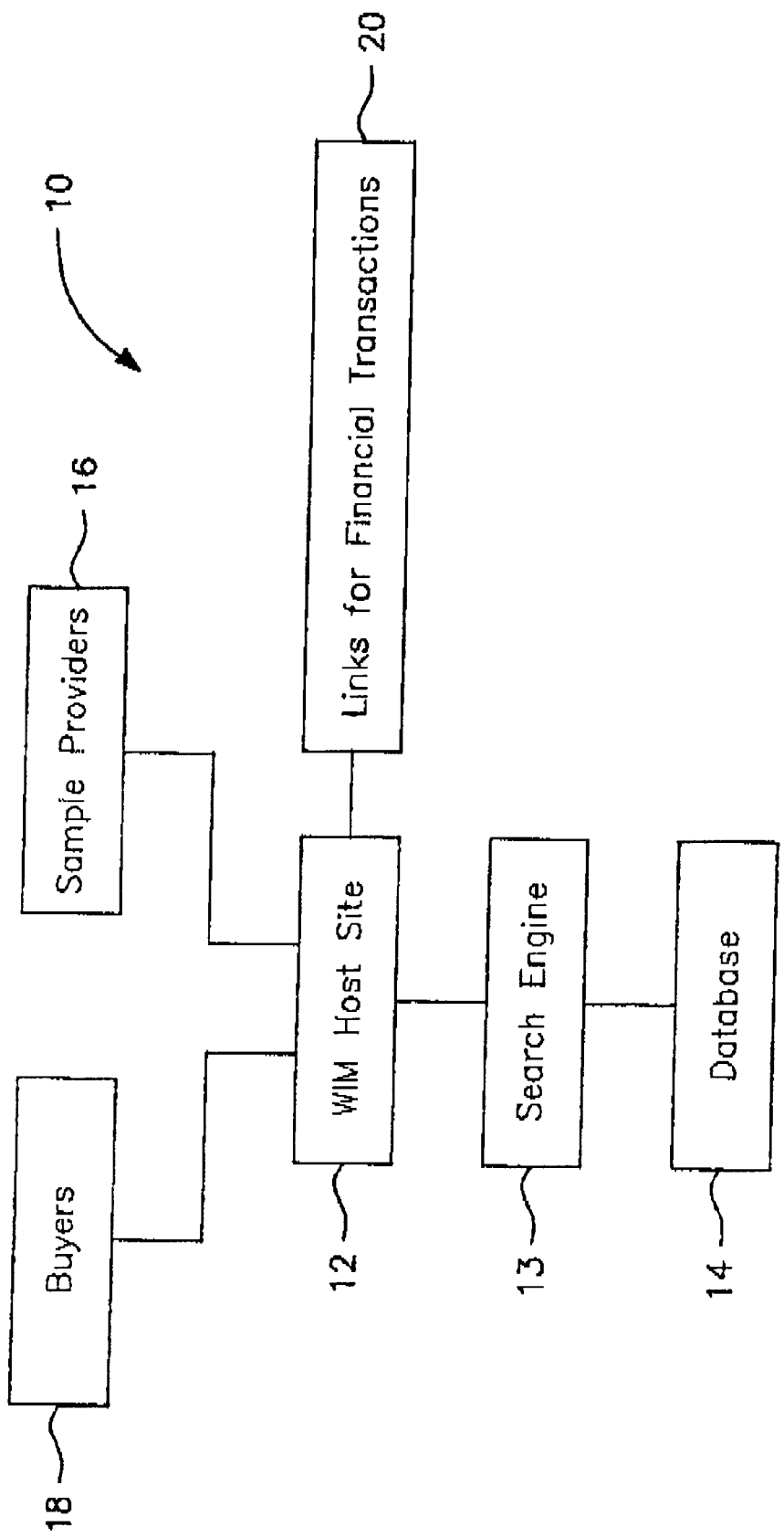
FIG. 1 is a block diagram of the web-integrated inventory management (WIM) system in accordance with the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

As illustratively shown in FIG. 1, the present invention is directed to a web-integrated inventory management (WIM) system, generally designated by the reference numeral 10. The system includes a central WIM host site 12 having a search engine 13 for accessing a database 14. Sample providers 16 and buyers 18 access the WIM host site 12 through a distributed computer network such as the Internet. The WIM host site 12 also has links for the financial transaction 20 necessary to complete inventory transfer.

The WIM system 10 provides means for buyers 18 and sample providers 16 to match their needs and available products, respectively. Registered sample providers and buyers may each initiate searches of the database 14 of the WIM host site 12 using the search engine 13. The result is maximum utilization of the available samples, and the enhancement of research and other clinical efforts to cure medical conditions.

The WIM host site 12 is prefer ably embodied as a web site accessible over the Internet. As such a site, the host site may be configure in a number of ways, as would be known by persons of ordinary skill in the art; the following general overview of the site is for illustrative purposes only.

Figure 2:
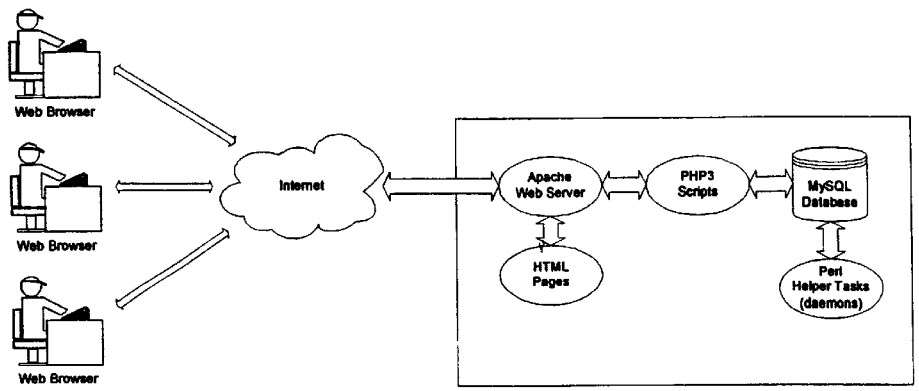
FIG. 2 is a diagram of a site architecture in accordance with one embodiment of the present invention.

FIG. 2 is an illustrative example of the site architecture. As shown in this example, web browsers provide the user interface, PHP3 scripts provide business logic, and a MySQL database provides data storage. A set of helper tasks or daemons written in Perl may be run on a regular basis to regenerate indices, update database flags, backup databases, etc., as scheduled by a Unix host system. Such a Unix system may be provided in a virtual server environment.

Figure 3:
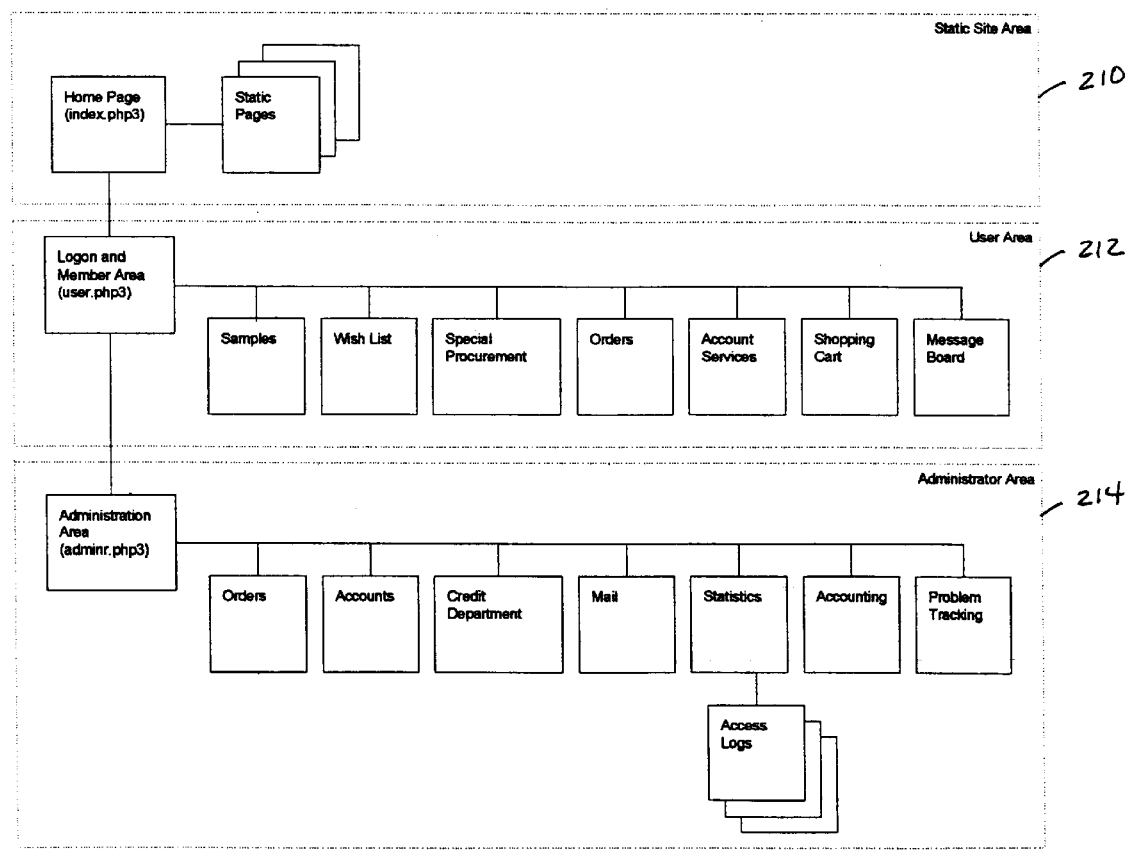
FIG. 3 is an illustrative overview of the contents of the WIM host site of FIG. 1.

FIG. 3 provides an illustrative overview of the host site and its contents. As shown, in preferred embodiment the host site includes a static site area 20, a user area 212, and an administrator area 214. The static area may be controlled using a main template script, e.g., index.php3. Although generated using a script, the area is referred to as static because it makes no use of the database.

A user.php3 script is the gateway to the dynamic part of the system. This script provides log-on services as well as the menu structure for the user area 212. Users belonging to the administrative group are able to enter the administrative area 214, which is representatively controlled through admin.php3 scripts.

Upon logging onto the WIM host site 12, the accessing user is greeted with a "Home" page which is within the static area 210. The "Home" page is the gateway to the site and provides the accessing user with an overview of the site's available information and procedures. Other pages or folders may be selected by clicking on the visible tabs and/or listed links as would be known by one of skill in the art. Pages may include, among others: "About Us", which summarizes information pertaining to the sponsoring host site; "Q & A", which presents frequently asked questions and the answers thereto; "Site Map", which summarizes the contents of the site with a listing of available page, that can be accessed by clicking thereon, and also provides a listing of support and purchasing information; "Contact Us", which provides address, phone and computer contact information of the host site sponsor, as well as promotional information; and "Register", which offers the accessing user the options of choosing to register as a sample provider, as a researcher, or as a guest. Each page, once accessed, contains multiple links to other pages, as is known to those of skill in the art.

The layout of the web pages can also accommodate advertising, particularly as pertaining to products and services relating to the biological and medical fields. Advertising may be incorporated throughout the pages or may be accessed through an advertising page or hyperlink, as desired. This option provides an excellent opportunity for product and service providers in the clinical research and related medical fields to target consumers having an interest in these specialized product and service areas.

All the data in the host site is stored in the database 14, which may be embodied as one or more MySQL databases. The database includes a plurality of tables; a representative arrangement of such tables for a preferred embodiment is provided in FIG. 4. Several other tables for various purposes are also maintained, and the tables are regenerated on a periodic basis.

Figure 4:
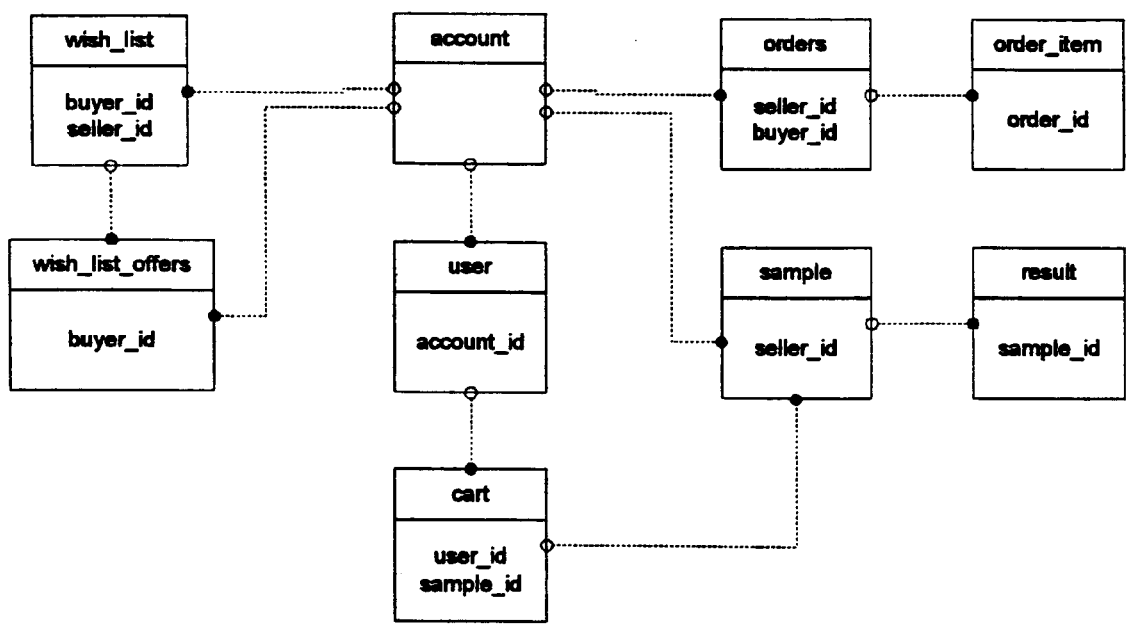
FIG. 4 is a representative arrangement of tables within the database of FIG. 1.

In the embodiment shown in FIG. 4, all tables in the database have a unique identifier field, called "id". This field is used to link related tables. For example, the user table has a field called account_id that is related to the account table id field. The seller_id and the buyer_id fields refer to the account id of the sample provider and buyer, respectively.

As shown in FIG. 4, the host site centers on the account table. This table contains all the information pertaining to a particular account. An account can have one or more users, samples, orders and wish list entries. The main user file of the account table indicates the users to which official correspondence will be sent.

The user table contains the users of the system. A user has one shopping cart, and belongs to one account. The sample table contains information about the samples. A sample belongs to one account. The results table contains specific information about products, drugs, or diagnosis associated with a sample. A sample can contain zero or more results.

Each user has an independent shopping cart, which is stored in the cart table. Researchers are allowed to search the system and add samples to the cart. For each item in the shopping cart, the user id of the buyer, the id of the sample, and the desired amount is stored in the table. Once the buyer wishes to place an order, the system creates an entry to the orders table, and the samples in the shopping cart are transferred to the order_item table. From this point on, the order and associated samples are tracked from the order_item table.

Figure 5:
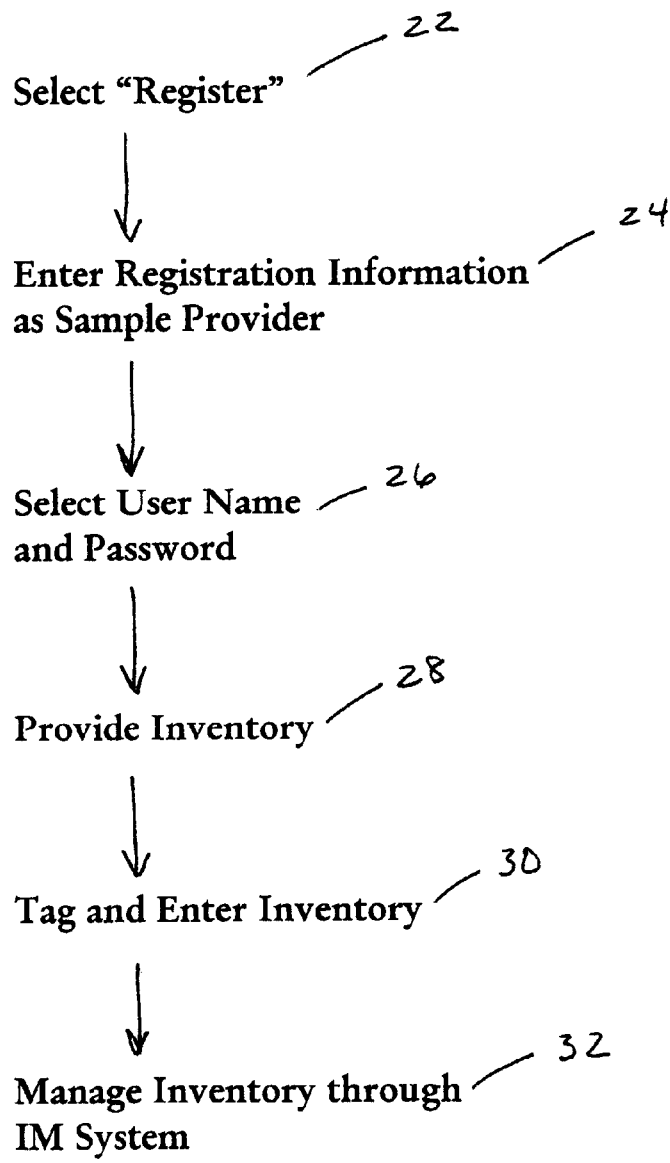
FIG. 5 is a flowchart of the process of sample provider registration within the WIM system of FIG. 1.

The database 14 resident at the WIM host site 12 contains an extensive inventory of biological samples belonging to a plurality of sample providers 16. This information is maintained in the sample table. In order to list sample inventory through the host site, each sample provider 16 must first register with the WIM system. This registration process is set forth in FIG. 5.

A sample provider wishing to register first accesses the WIM host site 12 using a web-enabled computer. In this document, "web-enabled computer" refers to a computer having all the necessary hardware and software, e.g., modem, browser, etc., correctly installed as would be known by one of skill in the art so as to enable the computer to be linked to a distributed computer network such as the Internet for access to and exchange of electronic information.

As used herein, a "web-enabled computer" is also understood to be enabled for electronic messaging such as transmission and receipt of email communications. However, it would be possible to implement the present invention without the use of email, relying instead on facsimile transmission, for example; such alternative embodiments are also covered by the present invention. However, in the preferred embodiments, email communication is utilized.

Upon accessing the WIM host site 12, the sample provider 16 selects the "Register" page 22 as an option from the "Home" page. The register option may be resident on a page accessed from the "Home" page, may be a selection button on the "Home" page, or may be made accessible to the sample provider in any other manner as would be known by those of skill in the art.

Upon access to the "Register" page, the sample provider selects the option to register as a sample provider and enters pertinent registration information 24. Such information should include at least the name of the organization, address and phone, URL, and email address. The registration information also requires entry of one of a CLIA number, an FDA registration number or a medical license number. (The CLIA number refers to a state license issued to laboratories under the Clinical Lab Improvement Act.)

Following entry of the administrative information, the sample provider enters a user name and password 26. During subsequent contacts with the WIM host site, the sample provider uses the specified user name and password. If the sample provider forgets the password, the WIM host site will prompt entry of the email address as provided during registration. The system will then send an email to the registered organization identifying the correct user name and password.

Once registered, the sample provider provides its inventory 28 to the WIM host site 12. Each sample is tagged and entered 30 into the database 14 of available samples. Samples are tagged by field to cross reference them in accordance with a variety of criteria. Sample fields may also be tagged for other purposes. Once the samples have been entered, sample providers may then manage their inventory through the WIM system 32.

The inventory management function of the present invention supports both sample providers wishing to list inventory for sale as well as companies with biological samples who desire inventory management capabilities but who do not have inventory they wish to sell. With particular focus on this latter group, in accordance with the WIM system of the present invention, such companies may license WIM system software. In a preferred embodiment, a copy of the WIM system software is loaded on one or more alternative secure web sites, separate from the WIM host site, and set up specifically for such inventory management support. Multiple inventories may, of course, be maintained at a single alternative site, with particular inventories accessed using a specific provider identification number or other code. Through such an alternative secure web site, licensed companies are able to access their inventory from any web-enabled computer, regardless of location. This capability also provides companies having a number of distributed offices, each of which may have a different internal computer system, with a centralized and unified means of tracking their company-wide in-house inventory that is simply not available in the prior art.

In an alternative embodiment, non-salable or maintenance inventory may be placed into the WIM host site database, but tagged to be non-viewable to prevent access by those parties searching the system to purchase samples. However, the preferred embodiment is to maintain sales inventory and maintenance inventory through separate WIM system sites. When used with specificity herein, "maintenance inventory" refers to biological inventory not offered for sale but being managed in accordance with the WIM system of the present invention. When not specifically identified as maintenance inventory, references to "inventory" are intended to include all kinds of inventory, whether being offered for sale or not.

As part of the inventory management function, whether through the WIM host site 12 or through an alternative web site supporting maintenance inventory management, the present invention further includes a bar coding capability for sample tracking. Through the WIM host site, or alternative site, electronic bar codes are provided to subscribing sample providers for each of their samples. These bar codes can include a range of information, as would be known by persons of skill in the art. The samples providers can download and print these bar codes using their own computer equipment and affix the resulting bar code labels on respective samples. Bar coding the samples enables automated sample retrieval and also enables the data identifying a particular sample to be transferred easily and electronically, whether within the sample provider's system or to an ultimate buyer of the sample. A buyer receiving a bar coded sample can use the information in the bar code to download the full record associated with the sample from the WIM host site, obviating the need to manually reenter the data into the buyer's computer. In that sample providers and purchasers may be dealing in hundreds of samples, this automation has tremendous value both in terms of time savings and the assurance of accuracy in sample information tracking.

Sample provider inventory information may be received in any number of formats dependent upon the sample provider's particular computer system, including as examples, spreadsheet, word processing, database, CVS comma delimited files, etc. Furthermore, a single sample provider may have multiple offices and, in many cases such as when the sample provider represents a merger of companies, each of these offices may use a different computer system. Without the present invention, such sample providers are virtually unable to search for samples within their own multi-office inventories, there being no commonality across their systems and no solution short of installing an entirely new system to unify all of their offices.

In accordance with the present invention, input data as received from sample providers are translated into a standardized, web-searchable format. In a preferred embodiment, input data is exported to a CVS file, which is then parsed by a customized Perl script which imports the data into the WIM host site database. This represents a significant benefit, not only to parties wishing to search the inventory for purchase, for also to the sample provider who needs to know the availability of in-house samples.

To describe a sample, the WIM host site database preferably uses two tables, a.sample table and a results table. The sample table contains a basic set of information that describes a sample and associated patient demographics. At a minimum, all samples contain one entry on the sample table.

The results table contains an arbitrary number of attributes that can be attached to a record in the sample table and which describe additional information about the sample beyond that placed on the sample table. In a preferred embodiment these attributes identify the search fields, but there does not have to be a direct correspondence between attributes and search fields. In general terms, the results table includes a label and a value. The label identifies an attribute or product, and the value represents a numerical value associated with the label. For example, the label may be "ferritin" with a value of 1.30. The search function performs searches over most of the fields of the sample table and over the label field on the results table.

According to the customization of the Perl script, customer record information is mapped to the host site database data record information. For each field provided in the customer data, the Perl script typically is configured to execute one of three options. The first option is for the script to map the customer sample field to one of the sample table fields. The second option is to append the customer sample field to the results table and associate that field with the sample table record for that sample. The third option is to ignore the field.

As part of the preparation of the customized import script, all fields that specifically identify the patient are tagged to be ignored. Fields so tagged are not copied into the WIM host site database. By stripping out personalized data, inadvertent disclosure is prevented, patient confidentiality is protected, and laboratories are encouraged to list more of their samples with the assurance that sensitive fields will not be listed with the sample.

In a preferred embodiment, only the laboratory identification (id) number or code given by the sample provider, and necessary for proper identification of the sample, is transcribed into the host site database. Furthermore, distribution of the laboratory id may be limited to the owner of the sample and to administrative host site personnel.

With large inventories, entry of samples is most efficiently transacted by downloading a computer file of the sample provider's database of inventory to the WIM host site. Inventory provided to the WIM host site through a downloaded computer file is processed by the WIM host site. This processing converts the data received from the often proprietary systems of sample providers into the centralized system of the present invention using the customized Perl script just described, or equivalent import technique as would be known by those of skill in the art.

Smaller inventories or individual samples to be entered may be added on-line by the sample provider through the WIM host site using the "Sample Inventory Management" page, as is described in greater detail hereinafter. In a preferred embodiment, the "Sample Inventory Management" page allows the sample provider to add a new sample, edit an existing sample, or list all samples.

To add a new sample, the "Add New Sample" option is selected from the "Sample Inventory Management" page to bring up the "New Sample" page, shown representatively in FIG. 6. As with all pages described herein, the "New Sample" page is exemplary only and is not intended to limit the on-screen presentation to the particular format shown.

In a preferred embodiment, the "New Sample" page includes links to other pages or folders which may be selected by clicking on the visible tabs or linking text, as would be known by one of skill in the art. These pages may include, among others: "Wish List", which allows the user to add a new wish, search the listed wishes, etc.; "Shopping Cart", which facilitates collection of samples for purchase; "Orders", which summarizes ordering information and procedures; and "Account Services", which provides a listing of account activity and status.

As may. be seen from FIG. 6, when new samples are entered into the database 14, each sample is identified according to a plurality of criteria, by fields, which describe or correlate with the sample. For example, instead of simply adding a sample to the database identified only as "blood", it is much more useful to researchers and others to know that the blood is of a particular type, came from a person of a particular race, demonstrates a particular abnormality, etc. Therefore, to maximize the utility of each sample, a plurality of criteria are specified for each sample, as appropriate to the sample type.

Representative categories of criteria to be identified for new samples as shown in FIG. 6 include sample information 15, patient information 17 and oncology information 19.

Sample information 15 may include volume, matrix, laboratory identification number and price. Whether or not the sample is a bulk sample may also be checked. Different or additional sample information may, of course, be used in accordance with the present invention.

Sample information may also include the designation of particular "products", with the embodiment shown in FIG. 6 illustrating two product designations, although additional product designations may also be included. For each "product", a product name, value, test outcome and method of test or test manufacturer may be entered. The "product" name may actually be directed to one of three subcategories, namely a product, a diagnosis or a drug, as shown. Additional details on sample information are included later herein.

Patient information 17 may include age, gender, race, patient ID, patient birth date, field of medicine, medical record available and doctor certified. Other or additional categories may also be included as appropriate. Additional details on patient information are included later herein.

Oncology information 19 may include site, stage, grade and status. Other or additional categories may also be included as appropriate. Further details on oncology information are included later herein.

Upon completion of data entry into the required, as well as any desired, fields, the sample is added to the inventory by clicking on the "Add" button 21.

To edit an existing sample, the sample provider can identify the desired, sample by a sample identification number, "sample ID"; a laboratory identification number, "lab ID"; or a patient identification number, "patient ID". The sample provider designates one of these categories, enters the appropriate number into the designated data entry field, and clicks on the "Search" button. The desired sample is then accessed by the search engine 13 from the database 14 for editing.

To list all samples, the sample provider can click on the "List all Samples" option. A list of samples belonging to the sample provider is displayed. A representative sample list is provided in Table I.

TABLE I

| ID | Lab ID | Matrix | Volume | Price |
| --- | --- | --- | --- | --- |
| 87888 | 12 | Plasma | 0.10 ml | 12.00 per sample |
| 87276 | 21215 | Serum | 12.00 ml | 2.00 per ml |
| 87294 | 32589 | Plasma | 0.20 ml | 12.00 per sample |
| 87279 | 96854 | Serum | 0.40 ml | 4.50 per ml |
| 87282 | 9696 | Heparin | 0.10 ml | 8.00 per ml |

As already discussed, the sample provider may manage inventory with the WIM host site, or alternative site, which is not available for purchase, if desired. However many, if not most, of the samples within the sample provider's inventory are typically available to buyers 18 for purchase.

Buyers include researchers and others having need of specified biological samples. For the purposes of this document, reference to "researchers" may be considered synonymous with reference to "buyers" and shall be used to indicate any party interested purchasing a sample through the WIM system 10.

Figure 7:
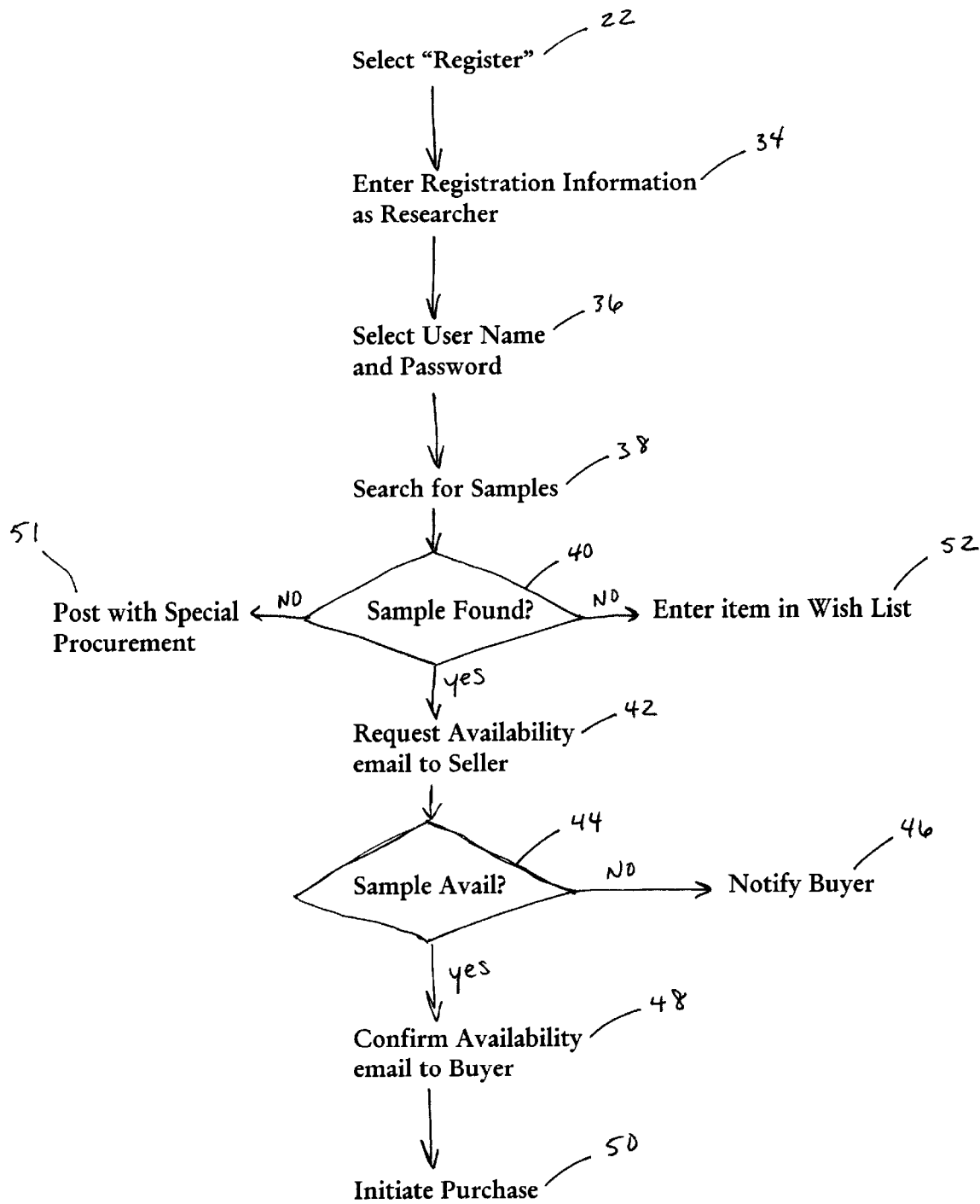
FIG. 7 is a flowchart summarizing buyer registration, sample search and sample purchase, in accordance with the present invention.
Figure 7:
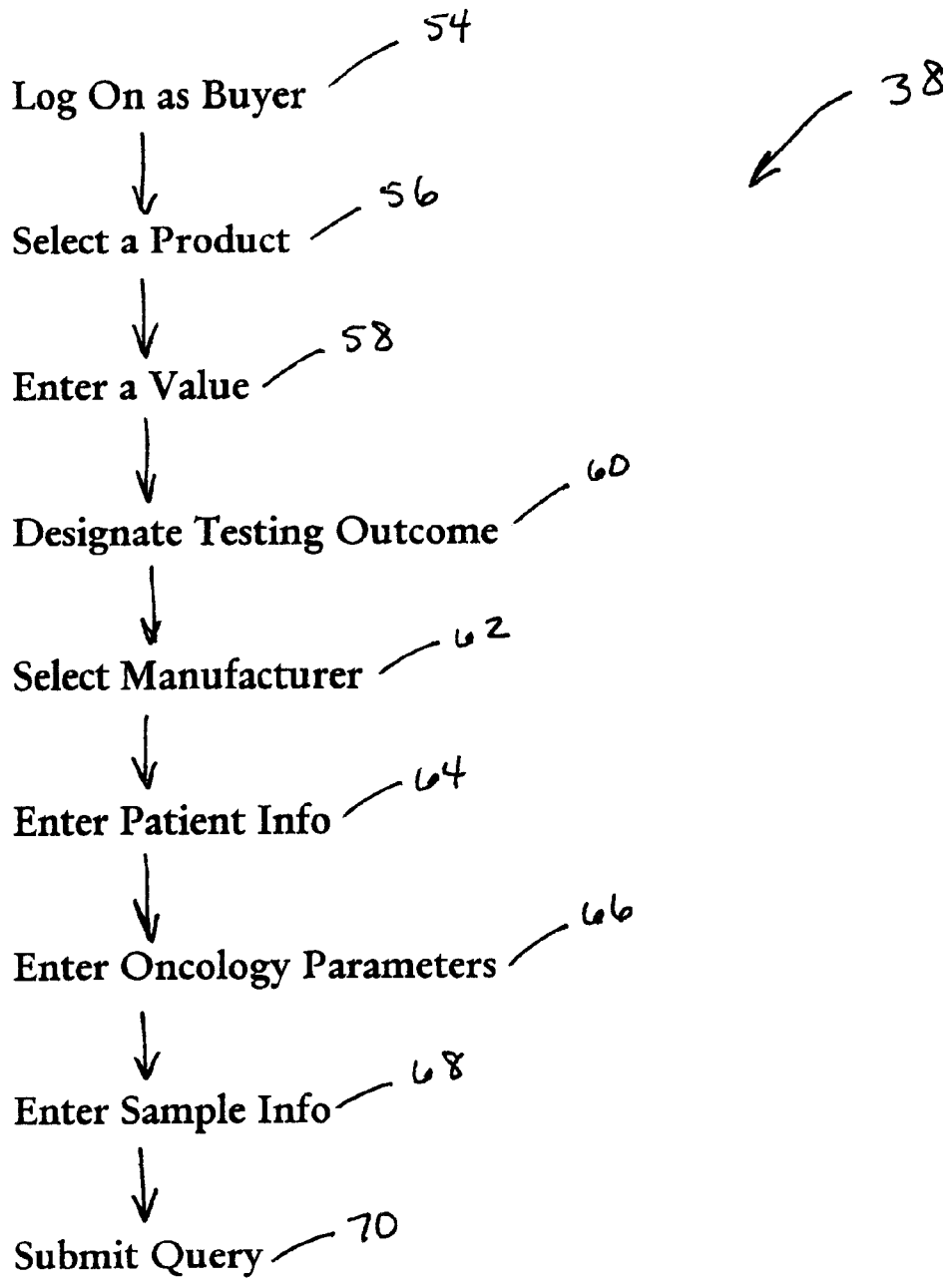

Buyers 18 register with the WIM host site 12 in order to be able to purchase the samples. The buyer registration process, along with a general overview of the search and sample procurement process in accordance with the present invention is set forth in FIG. 7.

A buyer wishing to register first accesses the WIM host site 12 using a web-enabled computer. In response to the "Home" page, the buyer selects the "Register" page 22. The register option may be resident on a page accessed from the "Home" page, may be a selection button on the "Home" page, or may be made accessible to the buyer in any other manner as would be known by those of skill in the art.

Upon access to the "Register" page, the buyer selects the option to register as a researcher and enters pertinent registration information 34. Such information should include at least the name of the buying organization, address and phone, URL, and email address.

Following entry of the administrative information, the buyer enters a user name and password 36. During subsequent contacts with the WIM host site, the buyer uses the specified user name and password. If the buyer forgets the password, the WIM host site 12. will prompt entry of the email address as provided during registration. The host site will then send an email to the registered buyer organization identifying the correct user name and password.

Once registered, the buyer may search for samples 38. A sample search may be conducted as a quick search or as a detailed search.

The quick search is a feature of the present invention that enables the buyer to type in what he or she is looking for specifically, without having to enter the range of individual search criteria required for a detailed search. To use the quick search feature, the buyer must enter a minimum of three characters representing a word, or part of a word, with which to search a product, diagnosis or drug field. For example, a buyer wishing to find a sample with various types of measles as the product would enter "mea". All relevant results would then be located and shown, regardless of whether they were input originally as a product, drug or diagnosis.

To conduct a detailed search, the buyer enters specified criteria describing particular parameters associated with the desired sample. Because each sample is cross referenced in accordance with a plurality of attributes, the buyer is able to designate with great specificity, if desired, the particular nature and attributes of the sample desired. This is a capability simply not available in the prior art where searching is often limited to designating a matrix or a matrix and one other parameter. Using the present invention, by contrast, samples may be identified in accordance with multiple parameters, with one present embodiment including 18 or more. The buyer can also limit the search to samples from a particular provider. Of course, values for all parameters need not be identified when entering or searching for a sample. But there are times when having the option of searching in accordance with a significant number of parameters enables highly specific research needs to be very particularly and efficiently met. A more detailed description of the detailed search process 38 is provided in FIG. 8.

If the search does not locate an appropriate sample 40, a negative search result is returned and the buyer may either post the desired item with special procurement 51 or enter the specified criteria for the desired sample to the wish list 52. Again, the potential for designating multiple parameters greatly increases the value of these options.

Special procurement is a feature of the present invention that allows the buyer to post his or her needs in written form without the aid or constraint of designated fields. The buyer is provided with a general data entry field and is directed to enter in detail the type and amount of samples desired. When data entry is complete, the buyer clicks on a "post request" button, or other analogous submission means, to post the request with the WIM host site. Once posted, the WIM host site is notified, and a procurement specialist team is assigned from the host site to facilitate in obtaining the posted samples.

Alternatively, the buyer may enter the item into the Wish List 52. As already mentioned, the wish list is a listing of desired, but currently unavailable, samples. The wish list may be described as a "wanted" section for use by both researchers and sample providers. Researchers use the list to post requests for samples that are not presently available in the inventory. Researchers can also review their own wish lists and make modifications as needed. A more detailed description of entry of items to the wish list is provided in FIG. 9. The wish list may also be searched by sample providers, as set forth in greater detail in FIG. 10.

If the search does locate an appropriate sample 40, the buyer may request availability of the sample 42. Responsive to a request for availability, the WIM host site generates and sends an email to the appropriate sample provider. If the request for availability requests availability of samples originating with more than one sample provider, the WIM host site splits the request according to sample provider and sends an email to each provider.

Each email identifies the sample or samples of interest and provides a hyperlink to the WIM host site. Each receiving sample provider clicks on the hyperlink and checks which sample or samples are available using a radio button or other equivalent means. To complete confirmation, the sample provider clicks on a "Confirm", or equivalent, button to send the confirmation to the host site.

Confirmation of sample availability is a valuable aspect of the present invention due to the fact that sample providers may sell their inventory through channels other than the WIM host site. When a sale is completed through the WIM host site, the database is automatically updated, concurrently or within a short time of the sale, removing from the listed inventory those samples which are no longer available. But since listing inventory with the WIM host site does not preclude the sample provider from transacting directly with other parties for sale of the samples, an item sold by the sample provider over the counter, for example, will not result in an automatic inventory update. Confirming availability enables the buyer to ensure that an advertised sample is indeed still in the sample provider's inventory.

If the desired sample is not available 44, the WIM host site notifies the buyer 46. If the sample is available 44, the WIM host site automatically generates and sends an email to the buyer confirming sample availability 48. A separate email is generated for each sample provider so that if three sample providers were polled for available samples, the buyer will receive three emails. The buyer may then initiate purchase 50 or cancel each order. A more detailed description of the purchase process is provided in FIG. 11.

Turning now to the search process as summarized in FIG. 8, the buyer begins by logging onto 54 the WIM host site using a web-enabled computer. Following log-on, he or she is presented with a data entry page for searching samples and may initiate a search. A representative sample "Search" page is provided in FIG. 12.

Figure 12:
FIG. 12 is an illustrative data entry screen for the sample searching process of FIG. 8.

As shown in FIG. 12, the "Search" page includes a quick search feature as well as a plurality of data entry fields, many of which correspond to the date entry fields shown on the "New Sample" page of FIG. 6. Data within these fields define the specified search criteria for a detailed search and are compared by the search engine to data entered in corresponding fields in sample inventory, so that detailed searching is conducted on a field by field basis. As previously discussed, the quick search feature allows the buyer to search according to a minimum of three characters entered into the quick search data entry field.

In the preferred embodiment and using the detailed search option, entry of data into certain data entry fields is required while others may be left blank. Every field containing data is compared with the corresponding field of a sample in inventory. To achieve a positive search result, i.e., a match between the search request and a sample in inventory, all entered data fields in the search request must correlate with corresponding data fields in a single sample in inventory. Data fields that are left blank in the search request do not limit the search, i.e., so long as the entered data matches corresponding data field data in a single sample in inventory, the fact that the single sample in inventory may have data entered in data fields corresponding to the blank fields does not prevent a positive search result.

The present invention may also be embodied such that required data fields must contain corresponding data between the search request and the inventory sample, while data fields that are not required will not prevent posting of a "possible" match. The posting of a "possible" match allows the buyer to review the inventory sample to determine if the parameters listed represent a sufficient match to enable the sample to be of use to the buyer. This posting of "possible" matches is an alternative embodiment. In the preferred embodiment, all entered data fields must match a sample in inventory in order for a positive search result to be obtained. If any of the entered data fields does not match a corresponding field in the compared sample in inventory, a negative search result is obtained.

The buyer begins by selecting a "product" 56. More specifically, the "product" may be one of three subcategories including a product, a diagnosis or a drug. With reference to the subcategory, product refers to a disease or a condition in a defined matrix. Other or additional subcategories may also be included as appropriate in accordance with the function and purpose of the present invention.

The buyer selects one of product, diagnosis or drug by clicking on the appropriate subcategory. If the buyer is not familiar with the search engine, he or she may click on the search button at this stage, and may thereafter narrow the search.

In a preferred embodiment shown in FIG. 12, two fields are provided for entry of a product, diagnosis or drug. Having two such fields allows the buyer to search for a product under two subcategories, e.g., under both product and drug, both product and diagnosis, or both diagnosis and drug.

Upon selection of a "product", an A–Z listing of the selected subcategory is displayed and a specific item within that listing may be selected. Clicking on the first letter of the desired item results in display of a list of items beginning with that letter. To select one of the items, the buyers clicks on the item, which is then automatically entered into the "product" name field.

"Product information", which in this document is intended to include and also refer to information pertaining to products, diagnoses or drugs, as applicable, further includes values, testing results and test manufacturer. Values represent a quantitative number for the product, diagnosis or drug, and may be entered 58 as absolute values, such as 5, 10, 150, etc., or they may be entered 58 as ranges of numbers, such as from 10 to 100. Testing results may be designated 60 as either a positive or a negative finding. Test result may also specify the qualitative or quantitative analysis by a specific manufacturer. Finally, test manufacturer may be selected 62 to obtain results based on a specific type of testing machine or to specify the diagnostic supplier of a specific assay. By clicking on test manufacturer, an A–Z listing of manufacturers is displayed. The manufacturer selected is automatically entered into the test manufacturer field.

The buyer then enters patient information 64. In the preferred embodiment, patient information includes age, gender, race, medical record available and doctor certified. Other or additional categories may also be included as appropriate in accordance with the present invention.

Age may be designated numerically as a specified number, as less than a specified number, as greater than a specified number, or as within a specified range. Age may also be entered more generally as "low" or "high". Gender and race have pull-down menus with available selections listed.

Medical record available allows the buyer to limit the search to results which have medical records available. Doctor certified allows the sample provider to limit the search to results which have been certified by a physician.

The buyer then enters oncology parameters 66. These may include site, stage, grade and status. The WIM search procedure may also be configured to include other or additional parameters as appropriate.

Finally, the buyer enters sample information 68. In a preferred embodiment, sample information includes volume, matrix, provider ID, sample ID, and medical field. Different or additional sample information categories may, of course, be used in accordance with the purpose and function of the present invention.

Volume is preferably designated as a specified amount and is given in units of either grams or milliliters. Optionally, the buyer may specify volume as less than a specified amount, more than a specified amount, within a particular range, or as "low" or "high".

Matrix may include, among others, bulk sera, bulk plasma, sera, plasma, cord blood, hair, saliva, semen, spinal fluid, stool, tissue, urine, whole blood, anticoagulants, and multiple matrix.

Provider ID typically designates the name of the provider. Sample ID refers to an identification number or code assigned to the sample during placement of the sample into the inventory of the database 14.

Medical field includes a listing of available medical field choices. A representative listing could include auto antibodies, cardiology, endocrinology, general chemistry, gynecology, hematology, infectious diseases, oncology, pathology, tropical diseases, dermatology, gastroenterology, musculoskeletal, urology, neurology, pediatrics, opthalmology, pharmacology, pulmonary and rheumatology, and geriatric medicine. The medical field listing is displayed by clicking on the down arrow adjacent the medical field data entry field.

Once entry has been made to all required fields, the buyer submits the search query 70. In the preferred embodiment, such submission is accomplished by clicking on the "Search" button on the "Samples" data entry page. The steps then proceed as already discussed in connection with FIG. 7 and are dependent upon whether or not a sample is found 40. As already mentioned, if a sample is not found 40 and a negative search result is returned, the buyer may post the desired item with special procurement 51 or may enter the desired item into the wish list 52.

Sample providers review wish list requests to see if any such requests match items in their inventory which are unlisted in the database or which are designated as private inventory. Upon finding a match, the sample provider may enter the matching, but previously unlisted, sample into the database 14. The match is detected during a next routine review by the WIM host site for matches between inventory and the wish list entries. Upon finding the match, the WIM host site generates an email to the requesting researcher notifying the researcher that a sample meeting their listed criteria is now available.

Alternatively, when a buyer places an item on the wish list, the WIM host site generates an email to subscribing sample providers identifying the wish information. One or more sample providers may respond with an offer to the buyer of a specified. sample, which is conveyed through the host site. Should the buyer accept the offer, the WIM host site notifies the sample provider of the acceptance. The sample provider then adds the sample to its inventory, and the WIM host site generates an email to the buyer listing the added samples. The buyer adds the samples to the shopping cart and the purchase sequence is initiated, as discussed in greater detail in connection with FIG. 11.

Figure 9:
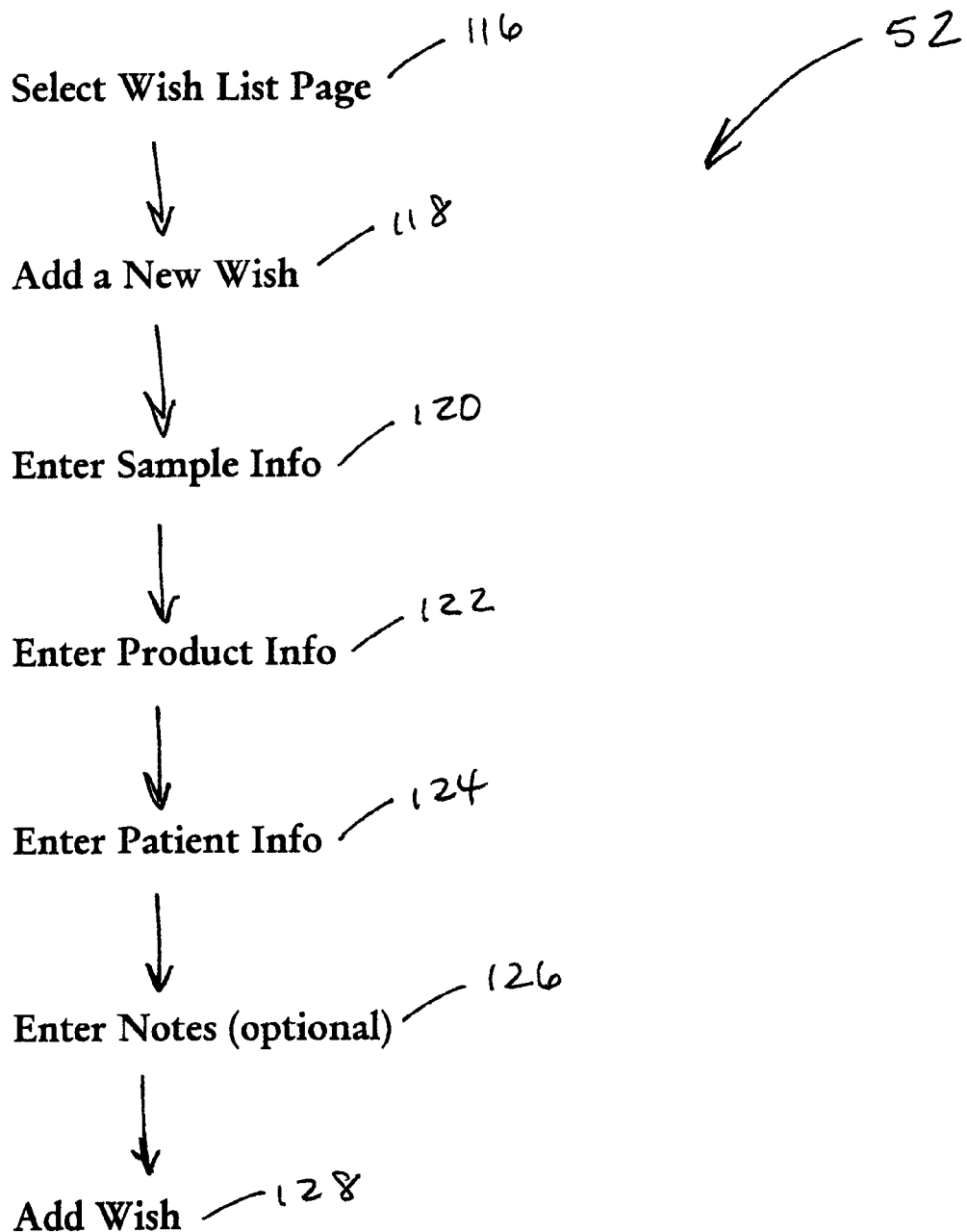
FIG. 9 is a more detailed flowchart of the entry of an item to the wish list process of FIG. 7.

The steps to be taken when adding an item to the wish list 52 are depicted in FIG. 9. The process begins by selecting the "Wish List" page 116 and then selecting the "Add a New Wish" page 118. The "Add a New Wish" page is a data entry page into which the buyer enters sample information 120, product information 122 and patient information 124. The buyer may also enter notes 126 as needed or appropriate.

In a preferred embodiment, sample information includes number of samples, price range, matrix and expiration date. Volume may also be included. Different or additional categories of sample information may, of course, be used in accordance with the present invention.

Number of samples may be designated numerically as a specified number, as less than a specified number, or as greater than a specified number. Number of samples may also be entered more generally as "low" or "high".

Price range may be designated numerically as a specified number, or as less than a specified number, and should include a price base, e.g., per sample, per unit, etc. Price range may also be entered more generally as "low" or "high".

Matrix specifies the form or substance of a sample. Matrix categories include whole blood, serum, urine, etc., and can also specify whether the sample is contained in bulk sera or is part of a multiple matrix. A multiple matrix may be comprised of multiple samples from the same patient, such as a whole blood sample and a urine sample. Generally, a multiple matrix is a collection of samples that belong to the same account, have the same lab identification number and different matrix. Samples may also be grouped into a collection known as a series. A series is a collection of samples that belong to the same account, have the same patient identification number and the same matrix.

Expiration date is typically entered by year, followed by month and day.

Volume may be designated numerically as a specified amount, as less than a specified amount, as greater than a specified amount, or as within a specified range. Volume may also be entered more generally as "low" or "high", and may be in units of milliliters or grams. Preferably the use of grams is limited to tissue samples.

In the preferred embodiment; "product" information may be designated according to three subcategories, namely product, diagnosis and drug, as has already been described. Other or additional categories may also be included as appropriate in accordance with the present invention.

The buyer selects one of product, diagnosis or drug by clicking on the appropriate subcategory. An A–Z listing of items within that subcategory is then displayed and a specific item may be selected. Clicking on the first letter of the desired item results in display of a list of items beginning with that letter. To select one of the items, the buyer clicks on the item name which is then automatically entered into the "product" name field.

In the preferred embodiment, patient information includes age, gender and race. Other or additional categories relating to patient information may also be included as appropriate in accordance with the present invention.

Age may be designated numerically as a specified number, as less than a specified number, as greater than a specified number, or as within a specified range. Age may also be entered more generally as "low" or "high". Gender and race have pull-down menus with available selections listed.

Once all required items have been entered, the buyer submits the new wish 128 to the wish list. In the preferred embodiment, such submission is accomplished by clicking on the "Add" button appearing on the "Add a New Wish" page.

The buyer may choose to review his or her wish list by selecting "My Wishes" from the "Wish List" page. The wishes are listed individually and specify, for each wish, an identification number, the date the wish was entered, the specified matrix, product name, and whether or not there is a match in the database. A representative wish list is provided in Table II. The researcher may review a particular wish in more detail by clicking on the appropriate identification number. The researcher may also delete a particular wish as appropriate, such as when a sample meeting the wish has been obtained.

TABLE II

| ID | Date | Matrix | Product | Match |
|----|------|--------|---------|-------|
| 286 | 14 Jan 00 | Serum | HSV | No |
| 285 | 14 Jan 00 | Serum | EBV | No |
| 284 | 12 Jan 00 | Whole Blood | Specific Proteins Assayed at 3 Different Levels | No |
| 277 | 10 Jan 00 | Whole Blood | Lyphilized Drugs Of Abuse Unassayed At Different Levels | No |
| 274 | 10 Jan 00 | Serum | Rubella | No |

The researcher may choose to search the Wish List. In a preferred embodiment, the researcher can search the Wish List for all wishes that have been posted for a specified number of days. For example, the researcher can specify a search of all wishes posted to the list within the last ten days. Alternatively, the researcher may search for wishes that have been on the Wish List for at least a specified number of days.

Figure 10:
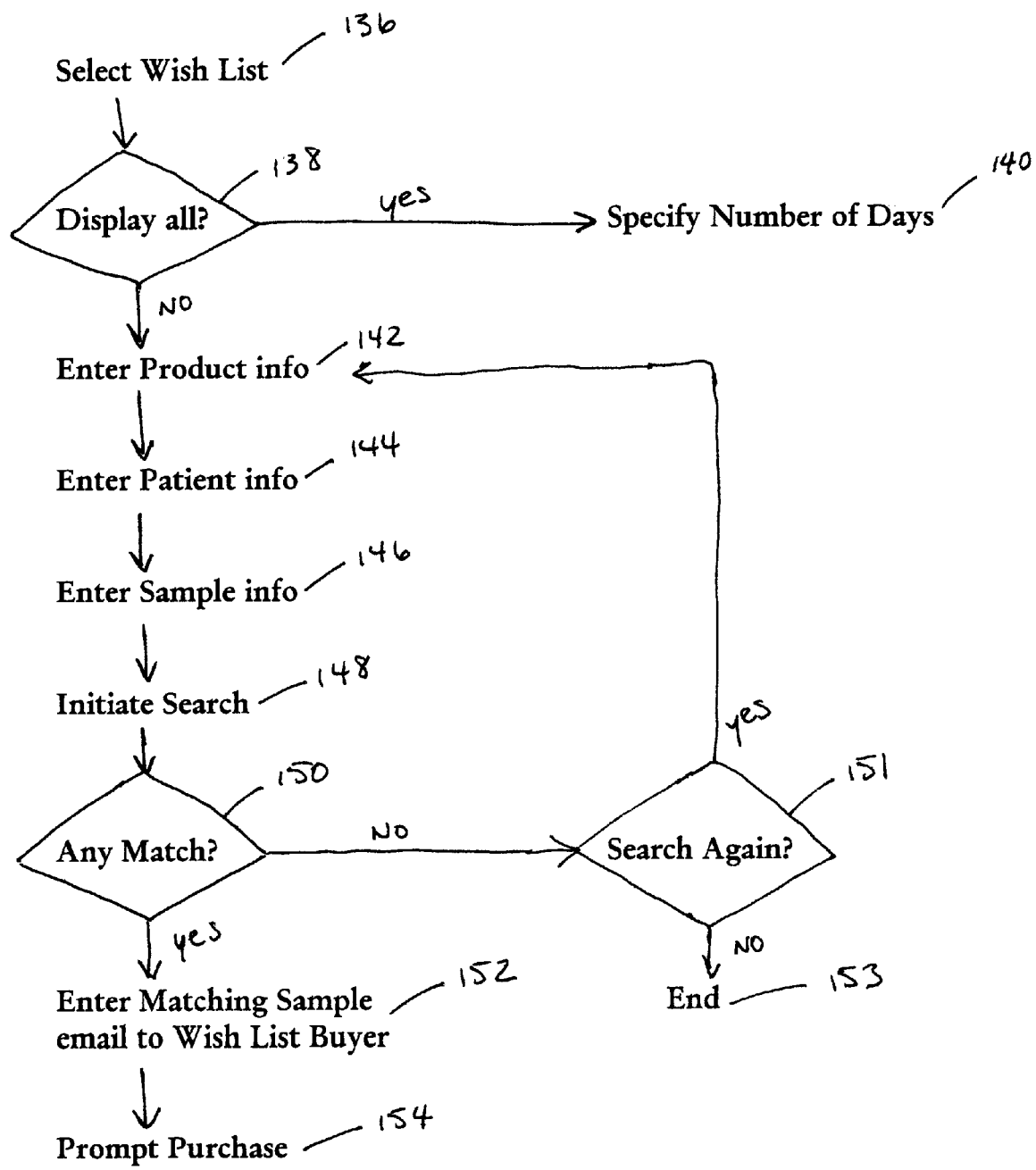
FIG. 10 is a flowchart summarizing sample provider searching of the wish list, in accordance with the present invention.

In addition to the buyer's access to the wish list, sample providers may wish to search the Wish List. Referring now to FIG. 10, the sample provider may search the wish list by first clicking on the "Wish List" file tab to display the "Wish List Search" page 136. By entering data into the "Wish List Search" page, the sample provider may search for and display all wishes 138 posted within a specified number of days prior to the search. The default is 30 days, but alternative periods may be selected by specifying a number of days 140. Alternatively, the sample provider may use the "Wish List Search" page to enter product information 142, patient information 144 and sample information 146, and initiate a search.

In the preferred embodiment, "product" information may be designated according to three subcategories, namely product, diagnosis and drug, as has already been discussed. Other or additional categories may also be included as appropriate in accordance with the present invention.

The sample provider selects one of product, diagnosis or drug by clicking on the appropriate subcategory. An A–Z listing of items is then displayed and a specific item may be selected. Clicking on the first letter of the desired item results in display of a list of items beginning with that letter. To select one of the listed items, the sample provider:clicks on the item name which is then automatically entered into the "product" name field.

Product information further includes values, testing results and test manufacturer. Values represent a quantitative number for the product, diagnosis or drug, and may be entered as absolute values, such as 5, 10, 150, etc., or they may be entered as ranges of numbers, such as from 10 to 100. Testing results may be selected as either a positive or a negative finding. Finally, results based on a specific type of testing machine may be obtained by clicking on test manufacturer to display an A–Z listing of manufacturers. The manufacturer selected is automatically entered into the field.

In the preferred embodiment, patient information includes age, gender, race, medical record available and doctor certified. Other or additional categories may also be included as appropriate in accordance with the present invention. Entry into these fields has already been described herein, and may be referred to as also applicable here.

In a preferred embodiment, sample information includes volume, matrix and notes. Different or additional sample information categories may, of course, be used in accordance with the present invention.

Volume is preferably designated as a specified amount. The database is searched for samples on the wish list entered in both milliliters and grams.

Clicking on "Matrix" reveals matrix categories that have been posted on the wish list. If the matrix being sought is not listed, then a sample with that matrix has not been posted on the wish list. If the matrix being sought is listed, then the appropriate selection is highlighted.

The sample provider may also search for a sample on the wish list based on the notes entered by the potential buyer posting the wish list item. For example, to search for a sample on the wish list with notes that include the word "sera", the word "sera" is typed into the notes field. Similarly, if searching for "bulk sera" those words are typed into the notes field. The search will identify samples using the exact combination of words appearing in the notes field.

Once all required field items have been entered, the sample provider submits the search query to initiate search 148. In the preferred embodiment, such submission is accomplished by clicking on the "Search" button near the bottom of the "Wish List Search" page.

If no match is found 150, the sample provider may choose to search again 151 using different criteria. If no additional searches are desired, the search ends 153.

If a match to the search. query is found 150, the sample provider may choose to enter the matching sample 152 into the database 14. Once entered, the match will be detected by the WIM host site during a next routine review of inventory versus wish list entries. The WIM host site runs such reviews on a regular basis and preferably at least every 24 hours. Upon detecting the match, the WIM host site automatically generates an email message to the buyer who posted the matching wish list entry. The email message notifies the buyer that a sample meeting his or her wish list specifications is available and prompts purchase 154.

Figure 11:
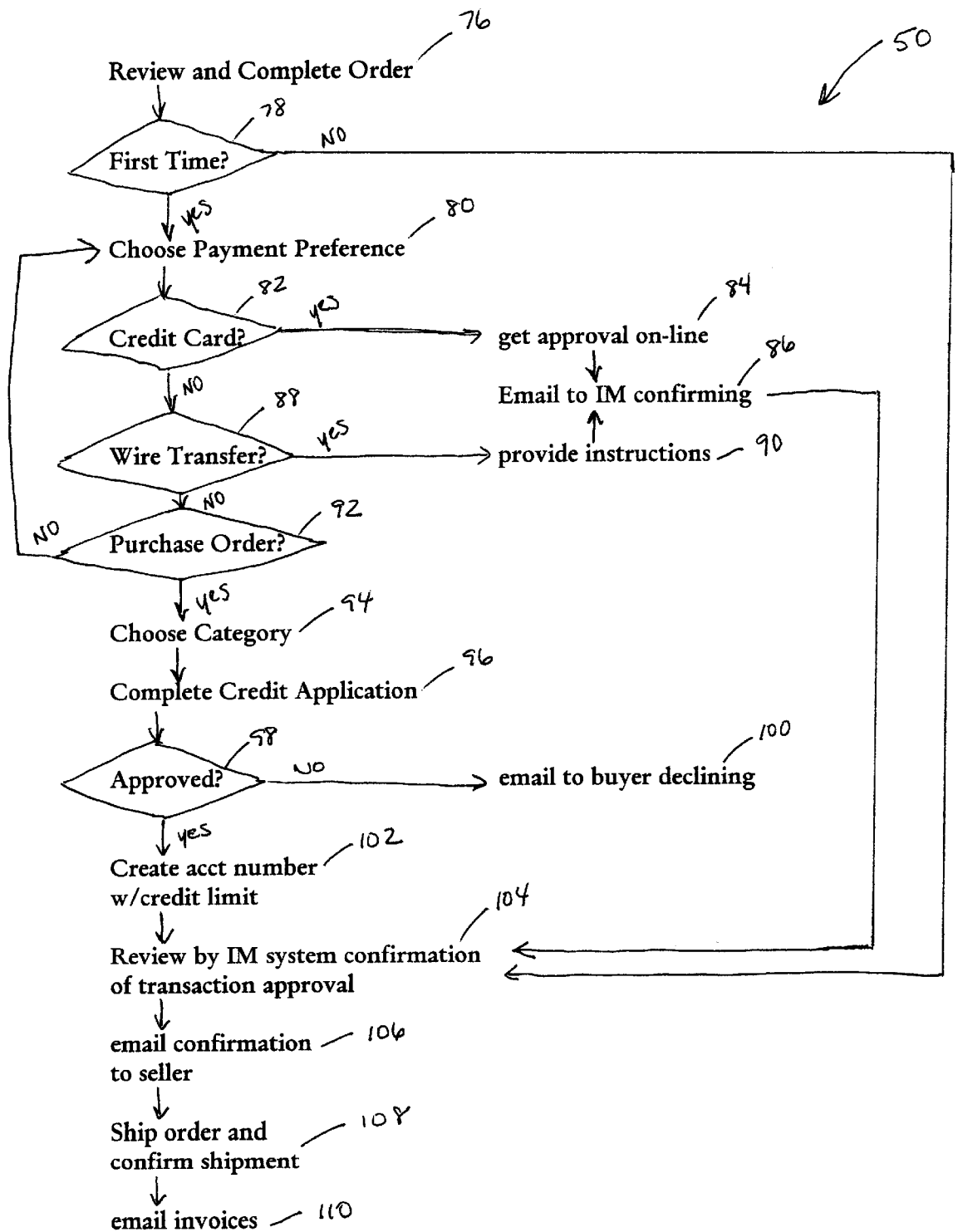
FIG. 11 is more detailed flowchart of the purchasing process of FIG. 7.

The steps to be undertaken when initiating a purchase 50 are set forth in FIG. 11. Once a sample has been identified and found to be available, the buyer reviews and completes an order 76 for the sample. Orders are stored in the database in the orders and order$_{13}$ item tables. The ordering process may include selecting the desired samples and placing them into a temporary holding status, such as an electronic shopping cart, from which items may be deselected if desired.

As noted earlier, the present invention may be configured to include advertising, most typically relating to the clinical research and medical fields. Display of some advertisements may be sensitive to the particular items being purchased, in a manner somewhat akin to the printing on grocery store receipts of coupons for the future purchase of particular items responsive to the buyer's currently purchased items. Therefore, in response to the purchase of a particular matrix, for example, products supporting or otherwise relating to that matrix may be presented to the buyer for inclusion in the shopping cart. The buyer is, of course, free to ignore the prompts and can proceed with purchase of the desired samples.

If the purchase represents the first time 78 the buyer has purchased, the buyer must choose a payment preference 80 and be approved for purchase.

If the buyer chooses to pay with a credit card 82, approval is typically obtained on-line 84 from an outside entity through the links for financial transactions 20. The outside entity sends an email 86 to the WIM host site confirming that approval has been granted or denied. Other means of obtaining approval may also be employed.

If the buyer chooses to pay with a wire transfer 88, the buyer provides transfer instructions 90 on a wire transfer instruction page, including bank coordinates for the wire transfer. The wire transfer instruction page also includes a date box to be filled in with the date when the wire was sent, the bank name and the country name. An email to the WIM host site confirms 86 the transfer.

If the buyer chooses to pay with a purchase order 92, the buyer chooses a category 94. In the preferred embodiment, the categories include Fortune 1000, universities and others, although other categories may also be specified in accordance with the present invention. The appropriate credit application is provided to the buyer responsive to the category selected; in the preferred embodiment, Fortune 1000 companies receive immediate credit approval upon registration.

Credit applications may be sent electronically or via facsimile, mailing, etc. The buyer completes the credit application 96, as applicable, and sends it to the WIM host site. At the WIM host site, received credit applications are placed in a credit application folder. In the preferred embodiment, this is a password protected folder maintained by the host site. Received credit applications are reviewed by personnel at the WIM host site. If the application is not approved 98, the WIM host site generates an email to the buyer declining 100 the buyer's request to purchase by purchase order.

If the credit application is approved 98, the WIM host site generates an account number with a specified credit limit 102 appropriate to the particular buyer. Account numbers and associated credit limits are placed in a credit accounts folder maintained at the WIM host site. The account number and credit limit of the approved buyer are then provided to a purchase authorization folder maintained at the WIM host site.

In the preferred embodiment, the purchase authorization folder is a password protected folder. All emails confirming transaction approval, whether from credit card 82, wire transfer 88, or purchase order 92, are directed to the purchase authorization folder. Transaction approval is reviewed by personnel at the WIM host site for confirmation 104 of approval.

If the transaction approval is confirmed, the buyer has been approved to make the requested purchase. During subsequent purchases, the buyer will be transferred directly to the purchase authorization folder for expedited transaction approval and is not required to repeat the initial credit authorization process for each purchase.

Upon transaction approval, the WIM host site then generates an email to the seller confirming transaction approval 106. The email may further include dollar amount, shipping address, handling fees, buyer shipping account numbers, etc.

Upon receipt of the confirming email, the seller ships the order and confirms shipment 108. The confirmation of shipment is directed to an orders shipped folder at the WIM host site and includes a tracking number for the shipment. In the preferred embodiment, the buyer designates a form of shipment, and related shipping information.

In response to shipment confirmation from the seller, the WIM host site generates emails to both the buyer and the seller 110. The email to the buyer includes an invoice with a description of the goods, total amount of the order, order number and shipment tracking number. The email to the seller is the same as the email to the buyer, but additionally includes a change of title credit slip for the specified invoice, less a transaction fee due to the WIM host site. A copy of each of the buyer and seller emails is retained in an invoice folder at the WIM host site. The invoice folder is preferably a password protected folder maintained by the host site.

As noted earlier, the WIM system may also be used by sample providers as an inventory management service for private inventory. Sample providers can maintain private virtual "shelf space" on the host site which they can access from anywhere in the world using a web-enabled computer. Using techniques similar to those set forth in connection with buyer searching and sample provider searching of the wish list, sample providers can use the search engine of the WIM system to search within, review and update their own inventories, all at minimal cost to the sample providers.

The foregoing descriptions and drawings should be considered as illustrative only of the principles of the invention. The invention may be configured in a number of ways, using a variety of software and hardware, and is not limited by the configuration of the preferred embodiment. Numerous applications of the present invention will readily occur to those skilled in the art. For example, the web-integrated inventory management system may be used to manage other types of inventory or as a clearinghouse for many kinds of specialty and non-specialty items. Therefore, it is not desired to limit the invention to the specific examples disclosed or the exact configuration and operation shown and described. Rather, all suitable modifications and equivalents may be resorted to, falling within the scope of the invention.

What is claimed is:

1. A method of implementing, with a central host site, an electronic commerce exchange for a web-integrated inventory of biological samples, the method comprising:

inputting identification information on a plurality of biological samples to a central host site inventory database, said plurality of biological samples belonging to at least one sample provider;

inputting a search request to the database for a biological sample, the search request containing specified search criteria;

searching the database for a biological sample matching the specified search criteria;

displaying a search result; and notifying, in response to a positive search result, a potential buyer of an availability of said biological sample.

2. The method as set forth in claim 1, further comprising, in response to a negative search result, the step of:

inputting a request for the biological sample to the central host site.

3. The method as set forth in claim 1, wherein said identification information for each biological sample includes data corresponding to specified fields, and said specified search criteria includes data corresponding to at least one of the specified fields such that the step of searching is conducted on a field by field basis.

4. The method as set forth in claim 3, further comprising, in response to a negative search result, the step of:

inputting a request for the biological sample to the central host site.

5. The method as set forth in claim 4, the step of inputting a request including inputting the specified search criteria to a wish list of desired but currently unavailable biological samples, each desired biological sample on the wish list being described by data categorized in accordance with the specified fields.

6. The method as set forth in claim 5, further comprising the steps of:

accessing a search page within the central host site;

entering, to the search page, data describing a non-inventory biological sample, the entered data categorized in accordance with the specified fields;

searching the wish list of desired but currently unavailable biological samples in the database for a desired biological sample described by data matching the entered data of the non-inventory biological sample;

displaying a wish list search result.

7. The method as set forth in claim 6, further comprising, responsive to a positive wish list search result showing a match between the desired biological sample and the non-inventory biological sample, the steps of:

inputting identification information on the non-inventory biological sample to the central host site to add the biological sample to the inventory database as a newly available biological sample;

comparing, by the central host site, the newly available biological sample to the wish list;

identifying, by the central host site, a match between the newly available biological sample and the desired biological sample; and generating, by the central host site, an electronic message to a potential buyer notifying the potential buyer of the newly available biological sample.

8. The method as set forth in claim 7, further comprising, responsive to the electronic message to the potential buyer notifying the potential buyer of the newly available biological sample, the steps of:

requesting an availability of the newly available biological sample;

generating, by the central host site, a first electronic message to a sample provider requesting confirmation of the availability of the newly available biological sample;

receiving, by the central host site, confirmation of sample availability;

generating, by the central host site, a second electronic message to the potential buyer confirming availability of the newly available biological sample; and initiating, through the central host site, purchase of the newly available biological sample.

9. The method as set forth in claim 8, further comprising the steps of:

receiving, by the central host site, a method of payment instruction;

granting, by the central host site, transaction approval;

generating, by the central host site, an electronic message to the sample provider confirming transaction approval;

shipping, responsive to transaction approval, the biological sample;

receiving shipment confirmation at the central host site;

generating, by the central host site, an electronic message with an invoice.

10. The method as set forth in claim 5, further comprising the steps of:

reviewing, by the central host site, newly available biological samples added to inventory;

comparing, by the central host site, the newly available biological samples to the wish list;

identifying, by the central host site, a match between at least one of the newly available biological samples and the desired biological sample; and generating, by the central host site, an electronic message to a potential buyer notifying the potential buyer of the at least one newly available biological sample.

11. The method as set forth in claim 1, further comprising, responsive to a positive search result showing a match between a biological sample and the specified search criteria, the steps of:

generating, by the central host site, a first electronic message to a sample provider requesting confirmation of the availability of the biological sample;

receiving, by the central host site, a response to the request for confirmation;

generating, by the central host site, a second electronic message to a buyer with a status on availability of the biological sample.

12. The method as set forth in claim 1, further comprising, responsive to a positive search result showing a match between a biological sample and the specified search criteria, the steps of:

requesting an availability of the biological sample;

generating, by the central host site, a first electronic message to a sample provider requesting confirmation of the availability of the biological sample;

receiving, by the central host site, confirmation of biological sample availability;

generating, by the central host site, a second electronic message to a buyer confirming availability of the biological sample; and initiating, through the central host site, purchase of the biological sample.

13. The method as set forth in claim 12, further comprising the steps of:

receiving, by the central host site, a method of payment instruction;

granting, by the central host site, transaction approval;

generating, by the central host site, an electronic message to the sample provider confirming transaction approval;

shipping, responsive to transaction approval, the biological sample to the buyer;

receiving shipment confirmation at the central host site;

generating, by the central host site, an electronic message to the buyer with a first invoice and an electronic message to the sample provider with a second invoice.

14. The method as set forth in claim 1, further comprising, in response to a negative search result, the steps of:

inputting the specified search criteria to a wish list of desired but currently unavailable biological samples as a new wish;

generating, by the central host site, an electronic message notifying subscribing sample providers of the new wish;

receiving, by the central host site, an offer from at least one subscribing sample provider of a biological sample responsive to the new wish;

generating, by the central host site, an electronic message notifying the buyer of the biological sample being offered;

generating, by the central host site, responsive to buyer acceptance of the offer, an electronic message notifying the sample provider of acceptance by the buyer;

adding the biological sample to the central host site inventory database;

generating, by the central host site, an electronic message to the buyer with the biological sample added;

initiating, through the central host site, purchase of the biological sample.

15. The method as set forth in claim 1, the step of inputting a search request including inputting a matrix and at least one sample parameter.

16. The method as set forth in claim 1, wherein the specified search criteria may include in excess of ten sample parameters, each sample parameter describing a particular characteristic of the biological sample to which the search request is directed.

17. A web-integrated inventory management system, comprising:

a central host site having a database and a search engine for accessing the database, the database containing information identifying a plurality of biological samples according to a plurality of specified data fields, said plurality of biological samples forming an inventory;

at least one sample provider registered with the central host site, said at least one sample provider owning biological samples listed within the inventory;

at least one buyer, said buyer accessing the central host site using a computer and searching the database with the search engine for a desired biological sample, the buyer specifying the desired sample in accordance with specified search criteria that include data corresponding to at least one of the specified fields such that the search is conducted on a field by field basis;

wherein, responsive to a positive search outcome, said central host site interfaces between an appropriate sample provider and said buyer to confirm sample availability and approve buyer credit, coordinating sample transfer from the appropriate sample provider to said buyer and effecting transfer of payment from said buyer to said appropriate sample provider.

18. The system as set forth in claim 17, said central host site further comprising a wish list of desired but currently unavailable biological samples, additions to said wish list being input by buyers following a search of the database in which no match was found between a desired sample and biological samples within the inventory.

19. The system as set forth in claim 17, wherein the specified fields include fields categorized as at least one of sample information, patient information and oncology information.

* * * * *